(12) United States Patent
Ho et al.

(10) Patent No.: US 6,605,363 B2
(45) Date of Patent: Aug. 12, 2003

(54) HIGH-DENSITY FUNCTIONAL SLIDE AND PREPARATION METHOD THEREOF

(75) Inventors: Chih-Wei Ho, Miaoli Hsien (TW);
Zu-Sho Chow, Hsinchu Hsien (TW);
Bor-Iuan Jan, Pingtung (TW);
Jia-Huey Tsao, Taoyuan (TW);
Chao-Chi Pan, Hsinchu (TW);
Wen-Hsun Kuo, Tainan (TW);
Yao-Sung Chang, Hsinchu (TW);
Cheng-Tao Wu, Tainan (TW);
Yu-Ching Liu, Taichung Hsien (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/836,322

(22) Filed: Apr. 18, 2001

(65) Prior Publication Data

US 2002/0028506 A1 Mar. 7, 2002

(30) Foreign Application Priority Data

Sep. 4, 2000 (TW) ........................ 89118070 A

(51) Int. Cl.⁷ ................................. B32B 9/04
(52) U.S. Cl. ................. 428/448; 428/429; 428/447; 428/524
(58) Field of Search ............... 428/447, 448, 428/524, 428, 429

(56) References Cited

U.S. PATENT DOCUMENTS

| | | | |
|---|---|---|---|
| 4,384,045 A | * 5/1983 | Ho et al. | 435/175 |
| 4,506,015 A | * 3/1985 | Ho et al. | 435/175 |
| 5,429,839 A | 7/1995 | Gravier et al. | |
| 5,919,626 A | 7/1999 | Shi et al. | |
| 5,922,534 A | 7/1999 | Lichtenwalter | |

OTHER PUBLICATIONS

Panda, A., & Singh, B.C.; Graft Copoiymerization of Acrylic Acid onto Biomedical Polyvinyl Alcohol Initiated By Ce(IV)–Glucose Redox System; Part 2; Polym.–Plast. Technol. Eng., 1996, vol. 35, No. 3, P 487–496.

Crowdhury, P., & Banerjee, M.; Graft Polymerization of Methyl Methacrylate onto Polyvinyl Alcohol Using $Ce^{4+}$ Initiator; Journal of Applied Polymer Science, 1998, vol. 70, P 523–527.

Chowdhury, P., & Pal, C.M.; Graft copolymerization of methyl acrylate onto polyvinyl alcohol using Ce(IV) initiator; European Polymer Journal 35, 1999, P 2207–2213.

Chan, M.A. et al.; Fiber optic oxygen sensor based on phosphorescene quenching of erythrosin B trapped in silica–gel glasses; Analytica Chimica Acta 408, 2000, P 33–37.

Pandey, P.C. et al.; A new glucose sensor based on encapsulated glucose oxidase within organically modified sol–gel glass; Sensors and Actuators B 60, 1999, P 83–89.

Chowdhury, P., & Pal, C.M.; Graft copolymerization of methyl acrylate onto polyvinyl alcohol using Ce(IV) initiator; European Polymer Journal 35, 1999, P 2207–2213.

* cited by examiner

*Primary Examiner*—Margaret G. Moore
*Assistant Examiner*—Michael Feely
(74) *Attorney, Agent, or Firm*—Venable LLP; Fei-Fei Chao

(57) ABSTRACT

The invention features a method for preparing a high-density functional slide by coating a sol-gel containing amine-group bearing silanes and a solution containing polyaldehyde groups onto an organic or inorganic substrate, respectively. The resulting slide is useful in the preparation of highly homogeneous functional-group slides and the high-density and high-efficiency bio-chip/microarray.

15 Claims, 6 Drawing Sheets

(6 of 6 Drawing Sheet(s) Filed in Color)

A  B

HIGH-DENSITY FUNCTIONAL SLIDE AND PREPARATION METHOD THEREOF

RELATED APPLICATION

The present invention claims the priority of Taiwan Patent Application No. 89118070, filed on Apr. 9, 2000.

BACKGROUND OF THE INVENTION

1. Field of the Invention

The present invention relates to a high-density functional slide and the preparation method thereof. More particularly, it relates to the application of a sol-gel containing amine-group bearing silanes and a solution containing polyaldehyde groups onto an organic or inorganic substrate, respectively, to form a high-density functional slide.

2. Description of the Related Art

There are many biomaterial immobilization methods that are available to immobilize biomaterial on different kinds of materials. For example, chemical activation, entrapment and crosslinking are well known in the art. However, these conventional methods suffer from many drawbacks, such as forming products of low stability and low activity and the inability of any one method to work well with a variety of biomaterial.

The conventional processes generally involve the treatment of a substrate surface with silanization, followed by the crosslinking reaction with biomaterials. In the silanization treatment, the surface of the substrate is activated based on its material, and then treated by a hydrophilic silane such as aminopropyltriethoxysilane (APTES). Afterwards, the crosslinking reaction is performed via a crosslinker such as glutaldehyde to immobilize biomaterials on the substrate. The shortcomings of the processes are long reaction time required for each of the steps (e.g. 4 hours or more), and low reaction efficiency. In addition, the homogeneity of the functional groups on the slide is uneven. This results in difficulties that the quality-control department has to overcome, and thus increases the production cost.

U.S. Pat. Nos. 5,919,626 and 5,922,534 disclose a method for attachment of unmodified nucleic acids to silanized solid phase surfaces. However, the surface of the solid phase is activated by a base, followed by bonding to epoxy-silane/amino-silane groups to facilitate the immobilization of nucleic acids/nucleotides. The disclosures of U.S. Pat. Nos. 5,563,056, 5,741,551, and 5,858,653 relate to the preparation of three dimensional, crosslinked matrices containing covalently immobilized chemical species and unbound releasable chemical species by photochemistry.

In the prior art, the co-deposition of silane and polyaldehyde groups onto a substrate in the sol-gel manner is not disclosed. Further, the application of the sol-gel onto an organic or inorganic substrate to form a high-density functional slide with an ultra-thin layer is also not disclosed.

SUMMARY OF THE INVENTION

It is therefore the primary object of the present invention to provide a method for preparing a high-density functional slide, comprising the steps of: (a) preparing a sol-gel of silanes in a first solvent; (b) coating said sol-gel onto a substrate; (c) removing the first solvent to form an interlayer on the surface of the substrate; (d) preparing a solution of polyaldehyde groups in a second solvent; (e) coating said solution onto the interlayer to form a polyaldehyde layer; and (f) removing the second solvent.

Another aspect of the present invention provides a high-density functional slide, comprising: (i) a substrate; (ii) an interlayer of a silane formed by coating a sol-gel of silanes onto said substrate; and (iii) a polyaldehyde layer formed onto said interlayer.

Still another aspect of the present invention provides a microarray having high-density functional groups for immobilization of a bio-molecule, comprising: (i) a substrate; (ii) an interlayer of a silane formed by coating a sol-gel of silanes onto said substrate; (iii) a polyaldehyde layer formed onto said interlayer; and (iv) a biologically active material, which is immobilized onto said polyaldehyde layer.

In one preferred embodiment of the present invention, the polyaldehyde polymer is prepared via the graft co-polymerization of polyvinylalcohol-based polyaldehyde. Therefore, the present invention also provides a polyvinylalcohol-based polyaldehyde graft copolymer, which is prepared by the following steps: (a) dissolving polyvinylalcohol in water to form a polymeric solution; (b) adding the monomer of allyl alcohol and acrolein to the polymeric solution under anaerobic conditions; and (c) adding ceric ammonium nitrate to the solution for catalysis.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

The present invention will be more fully understood and further advantages will become apparent when reference is made to the following description of the invention and the accompanying drawings in which.

DETAILED DESCRIPTION OF THE INVENTION

Figure 1:
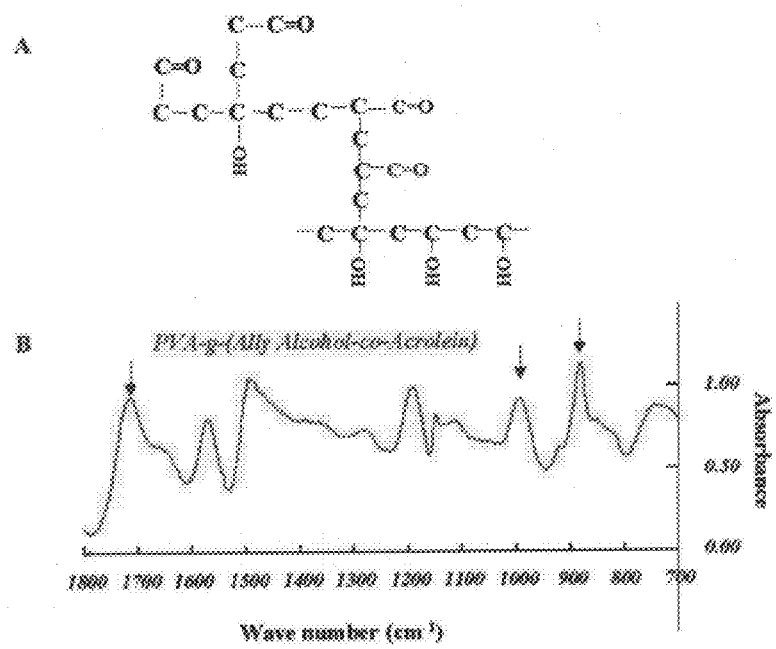
FIG. 1 is an IR spectrum showing the branched copolymer of the present invention with the distribution of polyaldehyde groups.

The present invention features a method for rapidly preparing a high-density functional slide by using a sol-gel process to form a layer of high-density functional groups, which facilitates the immobilization of bio-molecules to prepare a microarray carrying bio-molecules thereon, and elevates the immobilization efficiency of the bio-molecules. In addition, the amine-group density on the slide can be moderated by adjusting the ratio of each component during sol-gel synthesis. Thus, the subsequent coated polyaldehyde polymer can be properly bonded to and closely linked with the amine groups, thereby increasing the distribution of aldehyde density appearing on the slide and strengthening the bonding efficiency between the aldehyde groups and bio-molecules. The high-density functional slide prepared according to the present invention can make sure of the homogeneity of the functional groups on the slide. Further, the time for the production procedure is markedly shortened.

In accordance with the present invention, there is provided a method for preparing a high-density functional slide, comprising the steps of: (a) preparing a sol-gel of silanes in a first solvent; (b) coating said sol-gel onto a substrate; (c) removing the first solvent to form an interlayer on the surface of the substrate; (d) preparing a solution of polyaldehyde groups in a second solvent; (e) coating said solution onto the interlayer to form a polyaldehyde layer; and (f) removing the second solvent.

The term "high-density functional slide/microarray" used herein refers to the polyaldehyde layer coated on the silane interlayer that appears in the form of the steric structure of polyaldehyde polymer. Therefore, a huge number of aldehyde groups are exposed outside to further form a linkage with bio-molecules.

The term "sol-gel" used herein refers to the soluble sol-gel obtained via hydrolysis and condensation reactions in the water phase or organic phase.

According to the method of the invention, the type of the substrate is not limited, and can include an organic or inorganic substrate (i.e. substrate-independent). Organic substrates include a polymer polymerized by an organic molecule. Suitable organic molecules include, for example, a monomer of ethylene, propylene, ester, acrylic acid, acrylate, alkyl acrylic acid, or alkyl acrylate. Inorganic substrates include, but are not limited to silicon wafer, ceramic material, glass, or metal.

According to the preparation method of the invention, the substrate surface can be cleaned prior to coating sol-gel thereon to prevent the deposition of impurities or contaminants on the substrate surface. The cleaning step is performed by pretreatment with a solvent and/or sonication, based on the material of the substrate. Suitable solvents include, but are not limited to surfactant, water, alcohol, or acetone.

If an inorganic substrate, such as glass or a silicon wafer is employed, an activation step of the substrate surface can be carried out prior to coating an interlayer thereon to enhance the adhesion between the substrate surface and the interlayer. The activation step includes treatment of the substrate surface with a base solution so that the Si—OH structures can be formed on the substrate. Afterwards, the Si—OH structures contained in the sol-gel of silanes can react with those on the substrate, thereby enhancing the adhesion between the substrate surface and the interlayer. In addition, the use of organic substrates is also within the scope of the present invention (i.e. substrate-independent).

In accordance with the present invention, the sol-gel of silanes is prepared by the monomers of silane compounds dissolved in a suitable solvent (e.g. water or ethanol) via water-phase or ethanol-phase polymerization in the presence of an acidic or a basic catalyst (e.g. HCl or TMAOH). In this reaction, the monomers of silane compounds are selected from those with amine group(s), including, but not limited to aminopropyltriethoxysilane (APTES). During the synthesis of sol-gel, monomer silane compounds without amine group, such as tetraethoxysilane (TEOS), can be appropriately added so that the density of amine groups in the sol-gel can be adjusted. Thus, the subsequent coated polyaldehyde polymer can be properly bonded to and closely linked with the amine groups, thereby increasing the distribution of aldehyde density that appears and decreasing the steric hindrance on the slide. In addition, the aldehyde groups on the substrate will react with the amine-group bearing bio-molecules to be immobilized to form Schiff linkages (—CH=N—), as described below.

In one preferred embodiment of the present invention, the sol-gel of silanes is coated onto substrate via spin coating, followed by removing the solvent used for dissolving silanes via drying. Afterwards, a layer of polyaldehyde polymer is coated. Parts of aldehyde groups are bonded to the lower silane layer to form a stable structure, and others are exposed outside to form a functional layer with the distribution of aldehyde groups, which is useful for the subsequent binding of the biologically active materials.

Suitable polyaldehyde polymers include polyvinylalcohol-based polyaldehyde graft copolymer, which is synthesized by co-polymerization of allyl alcohol and acrolein using polyvinylalcohol as a stem nucleus and an appropriate amount of ceric ammonium nitrate as an initiator. In this reaction, the ratio of allyl alcohol to acrolein can be adjusted so that the co-polymerization can be carried out in the redox reaction system, and the aldehyde density can thus be controlled. In one preferred embodiment, the polyvinylalcohol-based polyaldehyde graft copolymer comprises 2–10%(w/v) polyvinylalcohol, 2–10%(v/v) monomer of acrolein and 1–5%(v/v) monomer of allyl alcohol.

However, those skilled in the art will be aware that the polyaldehyde polymer is not limited to the polymer synthesized by the method of the invention, other suitable aldehyde polymers can also be used. For example, the polyaldehyde polymer oxidized from polysaccharides using sodium periodate can be used. Suitable natural polysaccharides can include, but are not limited to dextran, agarose, etc.

The aforementioned sol-gels of silanes and polyaldehyde polymers can be prepared on a large scale, which are useful in the mass production of slide or microarray. In addition, those sol-gels are coated in the physical manner in lieu of the chemical reactions in each step of the conventional methods. The most advantageous is to make sure of the homogeneity of the functional groups on the slide, and to shorten the time required for the production procedure.

The method for coating the sol-gel onto a substrate is not limited, and is understood by one of ordinary skill in the art to which chemical engineering and semiconductor processes belong, to include spin coating, screen printing, roller coating, curtain coating, or dip coating, etc. In one preferred embodiment, the coating method used herein is spin coating, preferably at 3,000–6,000 rpm, and more preferably at 5,000 rpm.

After coating the sol-gel onto a substrate, the excess solvent is removed by means of, for example, vacuum evaporation, heating evaporation, or evaporation under reduced pressure, wherein the method of heating evaporation is carried out at a temperature not higher than 150° C. to prevent the matrix from being destroyed or to prevent undesired polymerization. The preparation of the slide of the invention is accompanied after the polyaldehyde layer is is coated and the solvent is removed.

In another aspect of the present invention, a high-density functional microarray is provided, comprising a biologically active material, which is immobilized onto the substrate described above. The immobilization is achieved by way of contacting the bio-molecules with the high-density functional slide of the present invention. In addition, the immobilization is carried out in a more efficient and stable way due to the steric polyaldehyde structures on the substrate. The interfacial immobilization reaction between the aldehyde groups on the slide and the amine groups of the bio-molecules (in which the amines are present in the bio-molecules itself or in a chemically modified entity) causes formation of interfacial Schiff-base bonds. In one embodiment of the present invention, Schiff linkages (—CH=N—) are subsequently treated by reductive amination, preferably by treatment with a reducing agent, for example, cyanoborohydride to form —$CH_2$—NH— bonds. Such reductive amination improves the strength of covalent immobilization.

Bio-molecules used as the biologically active material that are suitable for use in the invention include nucleic acid, oligonucleotide, peptide nucleic acid (PNA), antigen, antibody, enzyme, or protein. Stable amide linkages are formed after such bio-molecules react with the functional groups of the slide of the invention. As compared with the prior art in which the bonding is created via a two-step reaction (i.e., by the silane-based polymer and followed by adding a crosslinker such as glutaldehyde), the reaction is reduced to one-step reaction in the present invention. In one preferred embodiment, the time for the immobilization reaction is only 15 minutes, which is substantial reduction from that of the prior art, and the efficiency of immobilization is thus markedly increased.

Without intending to limit it in any manner, the present invention will be further illustrated by the following examples.

EXAMPLE

Example 1

Polyvinylalcohol-Based Polyaldehyde Graft Co-Polymerization 10 g polyvinylalcohol was heated to dissolve in 200 ml deionized water. The aqueous solution was placed in a 500 ml of round-bottom flask and nitrogen gas was purged to remove excess oxygen, and then the solution was returned to room temperature. To this solution, 10 ml acrolein monomer and 5 ml allyl alcohol monomer were added, and then the reaction system was sealed. After stirring for 15 minutes, 0.7 g ceric ammonium nitrate in 50 ml deionized water was added to the solution via a syringe for catalysis. The reaction temperature was maintained at 25° C. for 2 hours, and then the reaction was completed to give a milk-white solution of polyvinylalcohol-based polyaldehyde graft copolymer. The resulting solution was deoxygenated and sealed for storage.

Example 2

Structure Analysis for Coated Polyaldehyde Polymer 2 ml of polyvinylalcohol-based polyaldehyde graft copolymer prepared from Example 1 was coated onto a clean glass substrate over 4 square centimeters of area. The substrate was placed at room temperature and air dried to form a homogeneous film. The FT-IR analysis was performed for the resulting film to detect their IR spectra. The result is shown in FIG. 1.

Example 3

Preparation of Sol-Gel of Silanes with Amine Groups

Two parts of aminopropyltriethoxysilane (APTES) and two parts of tetraethoxysilane (TEOS) were dissolved in four parts of ethanol and placed in an ice bath. After stirring well, one part of 25% tetramethylamine aqueous solution was added as a catalyst. The reaction system was placed in an ice bath. After 2 hours of reaction, the reaction system was sealed and stored at room temperature, in which the product was used as the material for the subsequent slide preparation.

Example 4

Figure 2:
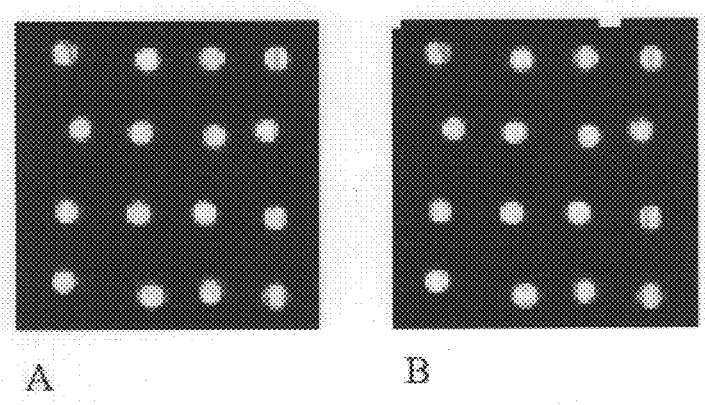
FIG. 2 is a diagram showing the fluorescence intensity of an inorganic slide (glass) coated with 20% APTES sol-gel as an interlayer and with 20% aldehyde polymer as a polyaldehyde layer: (A) after immobilization of labeled oligonucleotide probes; and (B) after washing with 5% SDS.

Preparation of High-Density Functional Slides (I) and Immobilization of Oligonucleotide Probe Glass substrates (inorganic substrates) were used in this Example. The sol-gel of silanes with amine groups obtained from Example 3 was compounded into 20% sol-gel with ethanol. 0.5 ml of 20% sol-gel of silanes with amine groups was dropped on the glass substrate and spin coated at 5,000 rpm. The slides were dried at room temperature to remove ethanol. In addition, the aqueous solution of polyvinylalcohol-based polyaldehyde graft copolymer obtained from Example 1 was diluted to the concentration of 0.5%(w/w). 0.5 ml of the copolymer was dropped on the above slide and spin coated at 5,000 rpm. The slides were dried at room temperature to remove solvent. A synthetic oligonucleotide probe Sp5 composed of 25 nucleotides in which the 3' end was labeled with fluorescence and the 5' end bearing amine group, was immobilized to the aforementioned slides to form Schiff linkages. The immobilization conditions were as follows: 0.5 $\mu$M of Sp5 in 2×SSC buffer (pH 7.0) was spotted on the slides and incubated at 37° C. for 1 hour. The slides were washed with 0.2% SDS for 30 minutes. The fluorescence analyses were performed for the slides with and without washing (control) to monitor the immobilization efficiency. The result is shown in FIG. 2.

Example 5

Preparation of High-Density Functional Slides (II) and Immobilization of Oligonucleotide Probe Polymethyl methacrylate (PMMA, organic) substrates were used in this Example, and other conditions such as slide preparation and probe immobilization were the same as Example 4. The results are shown in FIGS. 3(A) and 3(B).

Example 6

Figure 4:
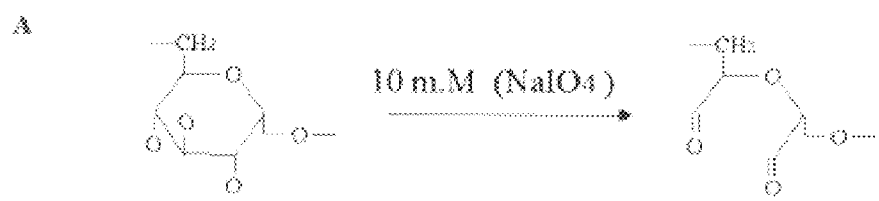
FIG. 4(A) is a diagram showing the structure of one glucose residue in the dextran, which is converted to two aldehyde groups by sodium periodate.
FIG. 4(B) shows the fluorescence intensity of a slide coated with 20% APTES sol-gel as an interlayer and with 0.5% dextran as a polyaldehyde layer, on which the labeled oligonucleotide probe is immobilized, followed by washing with 5% SDS.
Figure 4:
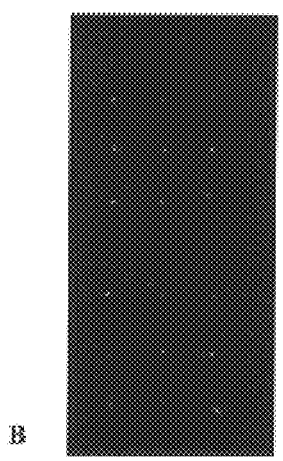

Preparation of High-Density Functional Slides (III) and Immobilization of Oligonucleotide Probe Glass substrates were used in this Example, and other conditions were the same as Example 4 except that the polyaldehyde polymer was replaced with dextran oxide. The concentration of the dextran oxide coated onto the substrate was 0.5%(w/w). The result is shown in FIG. 4.

Example 7

Figure 5:
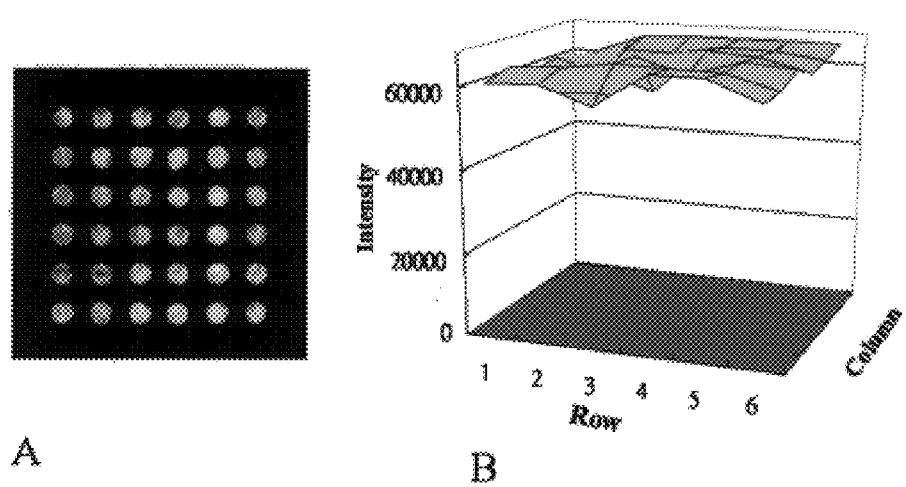
FIG. 5 is a diagram showing the relative standard deviation (R.S.D.) of the immobilization efficiency.

Homogeneity Test for Coating and Immobilization 0.5 μM of Sp5 (20 nl) was spotted mechanically on the slides to form a 36-spot array. After immobilization for 60 minutes under the same conditions as set forth above, followed by washing with 5% SDS for 30 minutes, the fluorescence intensity was analyzed for each spot, followed by calculation of the relative standard deviation (R.S.D.) of the immobilization efficiency. The result is shown in FIG. 5.

Example 8

Effect of Various Parameters on Immobilization of Oligonucleotide Probe

Figure 7:
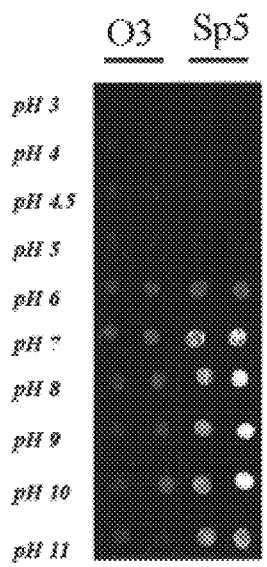
FIG. 7 is a diagram showing the effects of buffer pH on the immobilization efficiency of the high-density functional slide of the present invention.

Glass slides were used in this example to test the effect of parameters including time and pH on the immobilization of oligonucleotide probes. The immobilization conditions were similar to those in Example 4, wherein the probes used were Sp5 (as set forth above) and $O_3$ (without amine modification at the 5' end). The fluorescence intensity was measured at 10, 30, and 60 minutes to evaluate the relationship of immobilization efficiency with time. In addition, probes were immobilized under the environment of pH from 3 to 11 for 60 minutes to evaluate the optimal conditions for immobilization. The result is shown in FIG. 7.

Example 9

Hybridization with Specific Oligonucleotides

Figure 8:
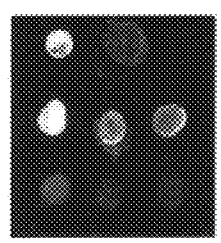
FIG. 8 is a diagram showing the fluorescence intensity after hybridization under various conditions.
Figure 8:
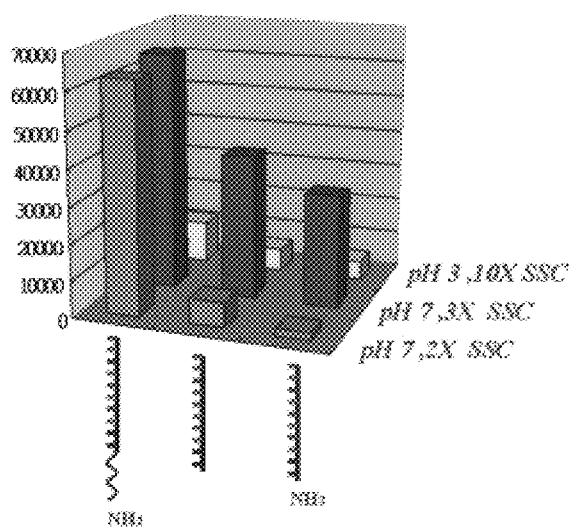

The slides used in this Example were the same as Example 4. The oligonucleotide Sp5 (without fluorescence labeling at 3' end) was used for immobilization followed by hybridization with the fluorescence bearing complementary sequence thereto. The immobilization conditions were 2×SSC, pH 7.0; 3×SSC, pH 7.0; and 10×SSC, pH 3.0, respectively, for 2 hours. The hybridization reaction was performed for 4 hours. The fluorescence intensity was analyzed to monitor the hybridization efficiency. The result is shown in FIG. 8.

Example 10

Stability of Polyaldehyde Layer on Slides

Figure 9:
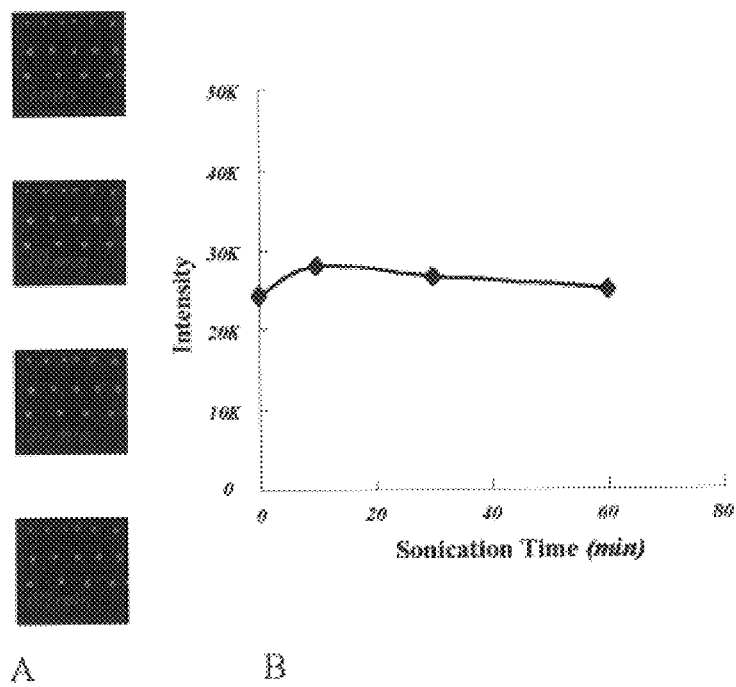
FIG. 9 is a diagram showing the stability test of the glass slide coated with polyvinylalcohol-based polyaldehyde graft copolymer of the invention.

The slides immobilized with fluorescent oligonucleotide probe were washed with 5% SDS, and monitored for fluorescence intensity and status of the polyaldehyde layer. The slides were then placed in an ultra-sonication device for physical treatment. The fluorescence intensity and surface of the polyaldehyde layer were monitored every 30 minutes. The result is shown in FIG. 9.

Example 11

Figure 10:
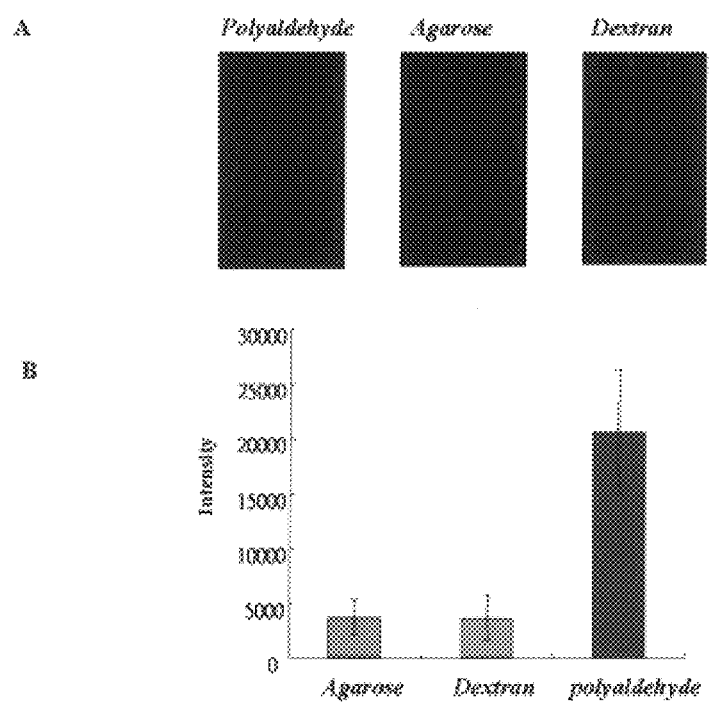
FIG. 10 is a comparative diagram showing the immobilization efficiency of polyaldehyde layer derived from various aldehyde-group sources, wherein (A) is a polyvinylalcohol-based polyaldehyde graft copolymer; (B) is agarose oxide; and (C) is dextran oxide.

Effect of Immobilization Efficiency on Various Sources of Polyaldehyde Groups 0.5 μM of Sp5 (0.6 nl) was spotted on the slides with various sources of polyaldehyde groups by microarray spotter. After immobilization for 30 minutes, followed by washing with 5% SDS, the fluorescence intensity was analyzed for each slide to evaluate the immobilization efficiency. The results are shown in FIG. 10 and FIG.. 11, respectively.

Referring to FIG. 1, the differences of the IR spectrum between polyvinylalcohol-based polyaldehyde graft copolymer and polyvinylalcohol are peaks with wave numbers of 1720 cm$^{-1}$, 1000 cm$^{-1}$, and 890 cm$^{-1}$. It is demonstrated that the polyaldehyde structures grafted on the polyvinylalcohol chain are prepared via polyvinylalcohol-based graft copolymerization using ceric ammonium nitrate as an initiator. Therefore, the preparation of high-density functional slides by application of the copolymer can be achieved. Biologically active materials with primary amine groups can thus be immobilized onto the slide of the invention by Schiff linkages due to the presence of aldehyde groups on the substrate surface.

FIG. 2 and FIG. 7 show the excellent immobilization efficiencies of oligonucleotide probe on the high-density functional slides of the invention in the buffers ranging from pH 7.0 to pH 11.0 over 30 minutes. After washing with 5% SDS for 30 minutes, an immobilization efficiency of higher than 75% is obtained according, to the fluorescence analyses. It reveals the stably covalent bonding formed quickly between the polyaldehyde layer and biologically active materials, thereby stably immobilizing bio-molecules onto the slides.

Further referring to FIG. 9(A) and FIG. 9(B), after long-time sonication and washing, the oligonucleotide probes immobilized on the slides of the invention are not peeled off according to the fluorescence and background analyses. In addition, the fluorescence intensity is not decreased with time, indicating an excellent stability of the polyaldehyde layer on the slides of the present invention.

Figure 3:
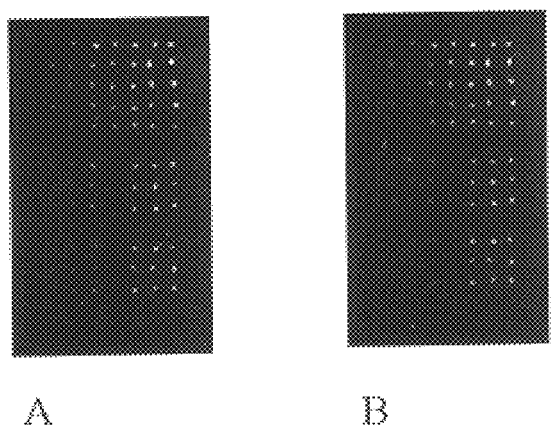
FIG. 3 is a diagram showing the fluorescence intensity of an organic slide polymethyl methacrylate (PMMA) coated with 20% APTES sol-gel as an interlayer and with 20% aldehyde polymer as a polyaldehyde layer: (A) after immobilization of labeled oligonucleotide probes; and (B) after washing with 5% SDS.

Comparing FIG. 2 (inorganic substrate) and FIG. 3 (organic substrate), it is shown that either organic or inorganic substrate is useful in the coating with sol-gel of silanes and polyaldehyde groups according to the preparation method of the invention. All these slides have excellent immobilization efficiency of bio-molecules, indicating the substrate is independent (i.e. the substrate can be organic or inorganic material) of the method of the invention.

In addition, the chemical structures shown in FIG. 4(A) represent one glucose moiety can be converted to form two aldehyde groups after suitable oxidation of sodium periodate, and can be the materials having the nature of high-density aldehyde groups distribution. From the result in FIG. 4(B), in which dextran oxide is used as the polyaldehyde layer, a stable immobilization is obtained in accordance with the method of the present invention. It suggests that besides the polyvinylalcohol-based polyaldehyde graft copolymer disclosed herein, one might use the oxidized natural polysaccharides as the polyaldehyde layer of the invention.

Homogeneity is one of the most important factors for the preparation of microarrays. Referring to FIG. 5, the homogeneity of the slide of the invention is excellent, which shows less than 4.5% relative standard deviation (R.S.D.) from 36 spots.

Figure 6:
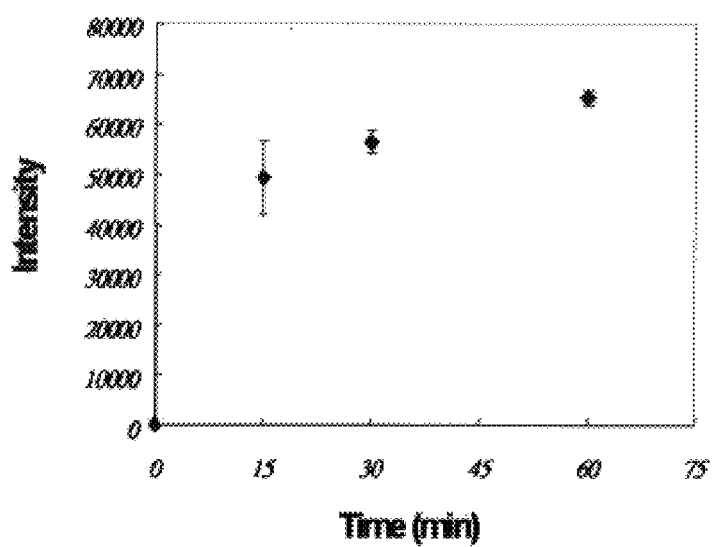
FIG. 6 is a diagram showing the time-dependent immobilization efficiency of the high-density functional slide of the present invention.

FIG. 6 illustrates the time-dependent immobilization efficiency of the high-density functional slide of the present invention. In the conventional method, about 4–16 hours are required for the immobilization of oligonucleotide probes. However, it takes only about 15 minutes for the same effect to occur on the high-density functional slide of the invention, wherein the immobilization efficiency reaches to about 75%. The time required is significantly shorter than the prior technique. With the increased time, the immobilization efficiency of the bio-molecules can be almost 100%. In addition, the bio-molecules immobilized on the slide is $10^{13}$ molecules per square centimeter according to analyses.

Referring to FIG. 7, under the conditions of pH 6 to 11, the preferred immobilization efficiency is obtained on the high-density functional slide of the present invention. Therefore, the slides prepared by the invention have better environmental tolerance, which is useful in the subsequent application. From other results (data not shown), if some organic compounds (e.g. triglyceride or formylamine) are added during the immobilization, the efficiency for the immobilization of the oligonucleotide probe is not affected. Thus, one may add such compounds for the subsequent uses depending on requirements.

Figure 11:
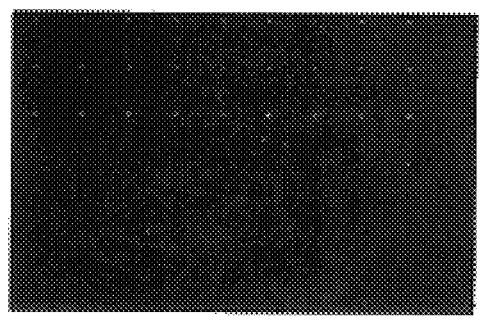
FIG. 11 is a comparative diagram showing the stability of the polyaldehyde layer derived from various aldehyde-group sources after hybridization, wherein (A) is a polyvinylalcohol-based polyaldehyde graft copolymer; (B) is agarose oxide; and (C) is dextran oxide.
Figure 11:
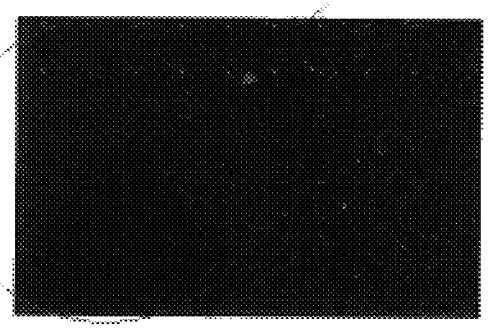
Figure 11:

Comparing the slides prepared from the natural polyaldehyde compound in Examples 6, 10, and 11, it is found the polyaldehyde layers thereon are markedly peeled off or chapped under the detector scanning (FIG. 11). It suggests the polyaldehyde layers formed by dextran oxide or agarose oxide are not stable, and are gradually peeled off after immobilization and/or hybridization. Referring to FIGS. 9–11, it demonstrates the polyaldehyde layers formed by polyvinylalcohol-based polyaldehyde graft copolymer of the invention have more mechanical strength and stability than those formed by natural polysaccharide of the prior art (see, for example, Victor A., et. al., Nucleic Acids Res., 28(12) e66:i–v, (2000).

From the non-limited examples described above, it is clear that the high-density functional slide prepared according to the present invention can make sure of the homogeneity of the functional groups on the slide. Further, the time for the production procedure is markedly shortened.

While the invention has been particularly shown and described with the reference to the preferred embodiment thereof, it will be understood by those skilled in the art that various changes in form and details may be made without departing from the spirit and scope of the invention.

What is claimed is:

1. A high-density functional slide, comprising:
   (i) a substrate;
   (ii) an interlayer of a silane formed by coating a sol-gel of silanes onto said substrate; and
   (iii) a polyaldehyde layer formed onto said interlayer.
2. The slide as claimed in claim 1, wherein the substrate comprises an organic or inorganic substrate.
3. The slide as claimed in claim 2, wherein the organic substrate comprises a polymer polymerized by organic monomers, wherein said organic monomers are selected from the group consisting of a monomer of ethylene, propylene, ester, acrylic acid, acrylate, alkyl acrylic acid, and alkyl acrylate.
4. The slide as claimed in claim 2, wherein the inorganic substrate is selected from the group consisting of silicon wafer, ceramic material, glass, and metal.
5. The slide as claimed in claim 1, wherein the polyaldehyde comprises a polyvinylalcohol-based polyaldehyde graft copolymer.
6. The slide as claimed in claim 5, wherein the polyvinylalcohol-based polyaldehyde graft copolymer is prepared by co-polymerization of allyl alcohol and acrolein using polyvinylalcohol as a stem nucleus.
7. The slide as claimed in claim 6, wherein the polyvinylalcohol-based polyaldehyde graft copolymer comprises an aldehyde density that is controlled by mixing different ratios of allyl alcohol to acrolein.
8. The slide as claimed in claim 1, wherein said sol-gel of silanes is polymerized by a monomer of silane in the presence of a catalyst.
9. The slide as claimed in claim 8, wherein the monomer comprises silane with amine group.
10. The slide as claimed in claim 8, wherein the monomer comprises mixtures of silane with and without an amine group.
11. The slide as claimed in claim 10, wherein the monomer of silane with an amine group comprises aminopropyltriethoxysilane (APTES), and the monomer of silane without amine group comprises tetraethoxysilane (TEOS).
12. The slide as claimed in claim 10, wherein the mixtures of silane comprise an amine density that is controlled by mixing varying ratios of silane with an amine group to silane without an amine group.
13. The slide as claimed in claim 12, wherein the amine groups on said interlayer are covalently bonded to part of the aldehyde groups on said polyaldehyde layer.
14. The slide as claimed in claim 13, wherein part of the aldehyde groups on said polyaldehyde layer are unbonded to the amine groups on said interlayer, said unbonded aldehyde groups being exposed to form a functional layer on said slide with a distribution of high-density aldehyde groups.
15. The slide as claimed in claim 14, wherein the unbonded aldehyde groups on the slide are bonded to an amine group of a bio-molecule to be immobilized by forming a Schiff linkage.

* * * * *